United States Patent [19]
Krynicki

[11] Patent Number: 5,704,379
[45] Date of Patent: Jan. 6, 1998

[54] DISPOSABLE FLOSSING AND DEBRIDER DEVICE

[76] Inventor: Richard T. Krynicki, 18838 N. 45th Ave., Glendale, Ariz. 85308-4409

[21] Appl. No.: 466,905

[22] Filed: Jun. 6, 1995

[51] Int. Cl.⁶ .................................................. A61C 15/00
[52] U.S. Cl. .................................................. 132/323
[58] Field of Search .............................. 132/323, 324, 132/325, 326, 327

[56] References Cited

U.S. PATENT DOCUMENTS

| | | | |
|---|---|---|---|
| D. 251,074 | 2/1979 | Schiff | D28/64 |
| D. 251,075 | 2/1979 | Schiff | D28/64 |
| 2,444,638 | 7/1948 | Dobbins | 132/324 |
| 3,699,979 | 10/1972 | Muhler et al. | 132/322 |
| 4,029,453 | 6/1977 | Campion, Jr. | 425/111 |
| 4,434,806 | 3/1984 | Givens | 132/323 |
| 4,531,530 | 7/1985 | Aiken | 132/323 |
| 4,615,349 | 10/1986 | Kukuruzinski | 132/324 |
| 4,736,757 | 4/1988 | Badoux | 132/324 |
| 4,982,752 | 1/1991 | Rodriguez | 132/324 |
| 5,014,725 | 5/1991 | Patscot et al. | 132/324 |
| 5,125,424 | 6/1992 | Eisen | 132/324 |
| 5,197,498 | 3/1993 | Stewart | 132/325 |
| 5,209,251 | 5/1993 | Curtis et al. | 132/321 |
| 5,213,428 | 5/1993 | Salman | 15/167.1 |
| 5,222,510 | 6/1993 | Zuehlsdorf | 132/323 |
| 5,246,021 | 9/1993 | Katz | 132/323 |
| 5,280,797 | 1/1994 | Fry | 132/323 |
| 5,388,600 | 2/1995 | Hart | 132/323 |
| 5,411,041 | 5/1995 | Ritter | 132/323 |

*Primary Examiner*—John J. Wilson
*Attorney, Agent, or Firm*—Marshall & Melhorn

[57] ABSTRACT

A dental hygiene device for removing plaque from the surface of teeth, both above and below and gumline. The disposable flossing device has an angled molded frame designed with a flossing end and a debrider end. The flossing end holds a tensioned strand of dental floss for cleaning around all teeth and specifically the molars. The debrider end utilizes a narrow debrider implement for the subgingival tracing around the teeth. The debrider implement optionally includes debriding grooves to assist in the tracing process.

20 Claims, 1 Drawing Sheet

DISPOSABLE FLOSSING AND DEBRIDER DEVICE

BACKGROUND OF THE INVENTION

1. Field of the Invention

This invention relates to an dental hygiene apparatus for removing plaque from the surface of teeth, both above and below the gumline. More particularly, this invention relates to a disposable flossing device having a molded frame holding a tensioned strand of dental floss for cleaning around all teeth and specifically the molars. The angled frame permits the gradual insertion of the floss between the teeth without forcefully impinging on the gums. The device additionally includes a debrider implement for the breaking up of bacterial colonies under the gumline.

2. Summary of Related Art

Dental professionals recommend the removal of dental plaque from the surface of teeth at a minimum of every twenty four hours. Plague is a sticky colorless substance which constantly forms in the mouth above and below the gumlines. Plaque, if not properly removed, will calcify and form a hardened material called tartar both above and below the gumline. Therefore, thorough cleaning around each tooth is required in order to prevent the calcification of plaque. The thorough cleaning above and below the gumline aids in the prevention of cavities and the formation of periodontal pockets.

A toothbrush will not sufficiently clean the area around each tooth. Dental professionals recommend daily flossing in order to remove plaque from around the gumline and between teeth. Floss and known flossing devices present problems in cleaning teeth, particularly the molars.

Present flossing devices do not sufficiently remove the plaque around the molars because of access problems associated with using the devices in the rear of the mouth. The limited access to the molars restricts the manipulation of the devices and therefore does not remove all of the plaque from the surface of the teeth. The devices can also cause soreness to the gums when the floss is forcibly inserted between the teeth. Additionally, the practice of tracing around each tooth to remove sub-gingival bacteria is not facilitated by the present inventions.

U.S. Pat. No. 5,014,725 to Patscot discloses a dental floss applicator having a planar support member with dental floss wrapped around the periphery of the planar member. The planar support member has notches cut into it at varying angles to create openings about the floss which allow the flossing of teeth. The patent discloses the use of a 45 degree angle and suggests a range of 30–60 degrees for use in cleaning around molars. The patent further discloses the use of fluoride in the floss and the use of biodegradable materials for the planar member.

U.S. Pat. No. 4,615,349 to Kukuruzinski teaches a disposable dental flosser having a fork like holder with two prongs. Dental floss is stapled between the two prongs. The patent discloses the use of medicated or flavored flosses for the apparatus.

U.S. Pat. No. 251,075 to Schiff is a design patent covering the ornamental design of a flossing device. The device has a two prong device with floss stretched between the prongs. One of the prongs is angled forward while the other projects downward. There are two griping members that extend to the side of flossing portion.

Additionally, the Dental Flossers™ marketed by Seneca Laboratories, Inc. has a two prong system with floss integrally formed between the prongs. Each of the prongs are positioned at 90 degree angles relative to the floss. The device includes a flat angled extension that serves as a handle for maneuvering the device. The user is directed to bend the extension forward into a different plane in order to reach the molars. The extension also has a pointed end that serves as a pick.

It would be advantageous to provide a dental flossing device that is capable of accessing the molars without any discomfort to the individual while improving cleaning efficiency.

A further advantage would be to provide a flossing device that permits the gradual introduction of the floss between the teeth without forcefully impinging on the gums.

It would be still a further advantage to have an improved means for gripping and controlling the device to improve the utilization and overall effectiveness of the device while reducing the hand fatigue of the user.

It would also be advantageous to provide a device that permits sub-gingival tracing around each tooth for the prevention of periodontal pockets and gum disease.

SUMMARY OF THE INVENTION

In accordance with the present invention, there is provided a disposable dental hygiene device for removing plaque from the surface of teeth, both above and below the gumline. The frame of the apparatus is designed with a flossing end and a debrider end. At the flossing end, the frame and the floss are positioned at an acute angle with respect to each other which thereby facilitates flossing around the teeth, specifically the molars. The debrider end utilizes a narrow tracing implement for sub-gingival tracing around the teeth.

The device comprises a linear frame having a base edge, a flossing end, and a tracing end. A control pad is integrally formed onto the frame in a co-planar manner.

A flossing head is integrally formed at the flossing end of the frame. The inner periphery of the flossing head and the control pad form a flossing arch. Floss is extended between the outer edge of the control pad to an outer edge of the flossing head across the open end of the flossing arch. The arch is designed to fit over and around adult teeth so that the floss directly contacts the gumline without the upper extremity of the arch contacting the teeth.

A first acute angle is formed at the intersection of the base edge extended and the floss line extended. This acute angle permits the use of the device around the molars. A second acute angle is formed at the intersection of the floss and the inner periphery of the flossing head. The second acute angle is greater than the first acute angle and creates a brake with the inner periphery of the flossing head. The brake prevents direct impingement of the floss onto the gums during insertion of the floss between the teeth. The floss and the tracing implement are manipulated around the teeth and gums by fingertip control of the control pad.

A debrider implement is formed at the debrider end of the frame. The debrider implement is used for the sub-gingival tracing around each tooth. A preferred embodiment of the invention includes debriding grooves in the debrider implement. The debriding grooves assist in the cleaning process by channelling the bacteria and other debris into the grooves for removal of the material from the user's mouth. Tracing, without such grooves, does not break up the bacteria and plaque from around the gumline.

It is an object of the present invention to provide a flossing device designed specifically to clean between the molars.

The molars are hard to reach with dental floss and with other flossing implements. The angled design of the present invention improves access to the molars directly from outside the mouth and allows flossing in the same plane as the gap between the teeth.

A further object of the present invention is to provide an angled brake that prevents the forceful insertion of the floss between the teeth. The gradual introduction of the floss eliminates the forceful impingement of the floss onto the gums and therefore prevents bleeding and soreness in the gums.

It is still a further object of the present invention to provide a flossing apparatus with a control pad that eliminates the hand fatigue of the user and assists in the manipulation of the floss. The reduction of hand fatigue promotes extended use of the cleaning tool and thereby results in improved dental hygiene.

A further object is to provide a debrider implement with debriding grooves at one end of the apparatus for sub-gingival tracing around each tooth. The tracing action loosens plaque and bacteria from underneath the gumline around each tooth and reduces the incidence of periodontal pockets. The debriding grooves assist in the removal of plaque and bacteria scraped away from the surface of the tooth during the tracing process.

BRIEF DESCRIPTION OF THE DRAWINGS

The above, as well as other advantages of the present invention, will become readily apparent to those skilled in the art from the following detailed description of a preferred embodiment when considered in the light of the accompanying drawings in which.

DESCRIPTION OF THE PREFERRED EMBODIMENT

Figure 1:
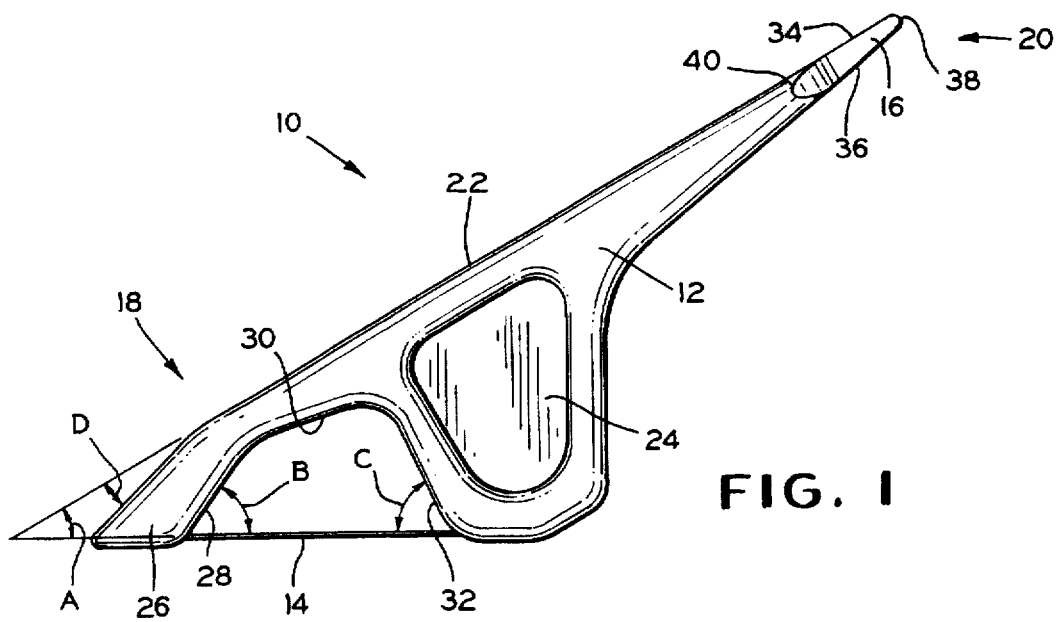
FIG. 1 is a side elevational view of the present invention.
Figure 2:
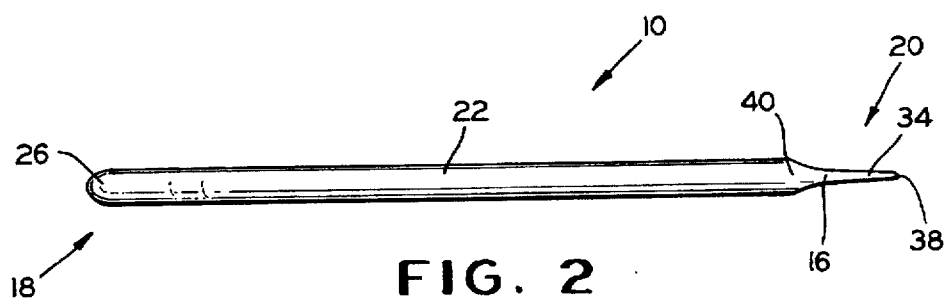
FIG. 2 is a top view of the apparatus of the present invention.
Figure 3:
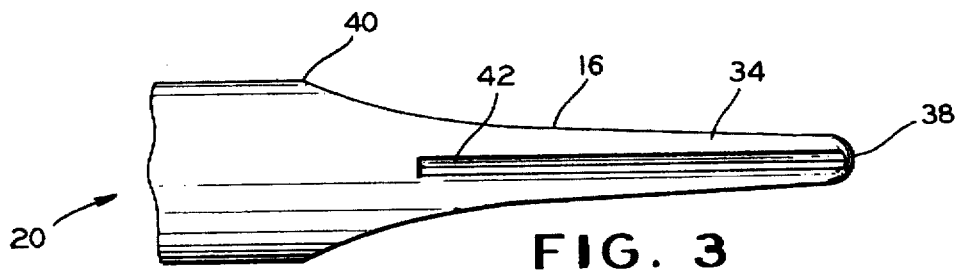
FIG. 3 is a top broken sectional view of the debrider implement with debriding grooves in an additional embodiment of the present invention.
Figure 4:
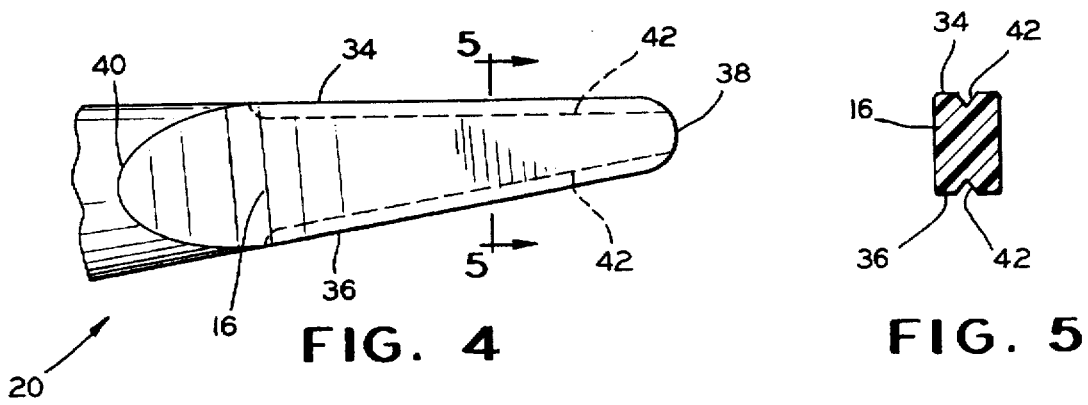
FIG. 4 is side broken sectional view of the debrider implement having debriding grooves.
Figure 5:
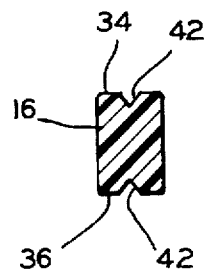
FIG. 5 is an end view of the debriding grooves in the debrider implement taken along datum 5—5 in FIG. 4.

Referring now more particularly to the drawings, there is illustrated generally in FIG. 1 the disposable flossing and debrider device 10 of the present invention. The device 10 has frame 12 which holds a section of floss 14. The floss 14 is used in removing plaque from the surface of teeth through the manipulation of the frame 12. Additionally, the frame 12 provides a debrider implement 16 for the sub-gingival tracing around each tooth.

The device 10 is made up of a linear frame 12 having a flossing end 18, a debrider end 20, and a base edge 22. The flossing end 18 and the debrider end 20 are integrally formed on opposing ends of the frame 12. The base edge 22 of the frame 12 extends linearly between the flossing end 18 and the debrider end 20.

A control pad 24 extends from the frame 12 in a co-planner manner opposite the base edge 22 between the floss end 18 and the tracing end 20. The control pad 24 is integrally formed or molded with the frame 12 and allows the firm grasping of the entire frame by the user. The control pad 24 can have various shapes or designs however it must be large enough to permit fingertip grasping of the frame by the user.

The flossing end 18 of the frame has a flossing head 26 which has an inner periphery 28 extending between the end of the flossing head 26 toward the control pad 24. The inner periphery 28 of the floss head 26 forms a flossing arch 30 with the inner periphery 32 of the control pad 24. The flossing arch 30 is deep enough and wide enough to fit over and around adult teeth.

A section of dental floss 14 extends between the flossing head 26 and an lower edge of the control pad 24 across the flossing arch 30. The floss 14 is preferably formed within the flossing head 26 and the control pad 24 during the molding of the frame 12. The technique of molding the frame 12 around the floss 14 permanently holds the floss 14 within the frame 12 and prevents the ends of the floss 14 from slipping during the flossing process. Alternatively, the floss 14 may be attached to the frame 12 after the frame 12 is manufactured. Adhesives or mechanical attachments are suitable for attaching the floss 14 to the frame 12 of the present invention.

In the present invention, there are several angles that are critical to the functionality of the device. These angles improve the use of the flossing implement and prevent soreness and discomfort to the user of the device.

A first acute angle A is formed at the intersection of the floss line extended and the base edge extended. The first acute angle A permits the use of the device to floss the molars. The angle is about 28–32 degrees. The molars are generally the hardest teeth to floss because of the limited access and the difficulty in manipulating the floss. The first acute angle A of the present invention permits the insertion of the floss from the side or corners of the mouth. The acute angle A allows the user of the present invention to floss the molars without opening the mouth to an uncomfortable position.

A second acute angle B is formed at the intersection of the floss 14 and the inner periphery 28 of the flossing head 26. The second acute angle B is generally greater than the first acute angle A because of the need to provide a flossing arch 30 within the flossing device 10 that will not interfere with the insertion of the floss 14 between the teeth. A more acute angle would create a shallow inner periphery 28 in the flossing arch that would strike the teeth and prevent the floss 14 from reaching the gumline. The acute angle B serves as a brake to prevent impingement of the floss 14 onto the gums during insertion of the floss 14 between the teeth.

Alternatively, a third acute C angle may be formed at the inner periphery 32 of the control pad 24 and the floss 14. This angle permits the inner periphery 32 of the control pad 24 to serve as a second brake for the present invention.

A fourth acute angle D is optionally formed by the downward extension of the flossing head 26 from the base edge 22. The fourth acute angle D brings the flossing head 26 closer to the control pad 24 thereby requiring less floss 14 and improving the ability to manipulate the floss 14 while inserted between the teeth. The shorter flossing end 18 reduces the length of the extension into the mouth and keeps the flossing head 26 near the teeth.

In general, the floss 14 used in the present invention is a woven nylon. The integrally molded floss 14 within the frame 12 permits the use of a loose weave nylon versus a tight weave nylon. The loose weave nylon offers specific benefits over tight weave nylon in that the loose nylon separates into small single strands to accommodate entry into the tightest openings between teeth. Additionally, the loose weave allows the floss to splay giving a wider cleaning profile.

A debrider implement 16 is formed at the debrider end 20 of the frame 12. The debrider implement 16 has an upper and lower edge 34, 36 and an end point 38. The implement 16 narrows from the base edge 22 of the frame 12 at a shoulder 40. The implement 16 is used for sub-gingival tracing to remove plaque and break up bacterial colonies from the surface of the tooth below the gumline. Additionally, the debrider implement 16 may be utilized as a pick to remove material lodged between teeth. The debrider implement 16 is narrower than the frame 12 in order to permit the end point 38 to be inserted between teeth and under the gumline. The sub-gingival tracing removes bacteria and plaque from underneath the gumline and reduces the formation of periodontal pockets and the development of gum disease.

The present invention alternatively includes debriding grooves 42 on the debrider implement 16. The debriding grooves 42 are narrow grooves formed in the upper and lower edges of the debrider implement. The debriding grooves extend from near the shoulder of the implement to the end point. The debriding grooves 42 provide a means to break up and carry away bacteria and plaque as the material is loosened and scraped away from around the teeth and under the gumline during the tracing process.

The frame 12 is generally an injection molded polymer, such as polyethylene or polystyrene. Any polymer that forms a substantially rigid frame is suitable for use with the present invention. Preferably, a biodegradable polymer is used to lessen the impact of the disposable device on the environment. Biodegradable polymers are known in the art and are suitable for forming the frame of the present invention.

Alternatively, the frame 12 of the present invention may be made of cardboard or suitable rigid paper products. A cardboard frame may be pressed or cut with a die to form a rigid frame. The floss could then be attached with an adhesive or a mechanical attachment.

Having set forth a description of the structure of the present invention, the use and function of the disposable flossing and tracing device may now be described with particular reference to FIGS. 1–5.

In the present invention, the use of the device 10 for flossing requires gripping the control pad 24 first with the finger tips with the flossing head 26 extending outward away from the hand. The size and shape of the control pad 24 provides an adequate gripping surface and permits fingertip manipulation of the entire device 10 without causing fatigue to the user's hand, which may facilitate longer and more thorough cleaning sessions.

The floss 14 is inserted between the teeth by first using the brake created by the second acute angle B. The brake prevents direct impingement of the floss 14 into the gums upon insertion of the floss 14 between the teeth. The brake is utilized to gradually slide the floss 14 between the gap of the teeth until the floss 14 is in the cleaning position at the gumline. The brake is positioned against the inside edge of the gap between teeth with the floss partially inserted into the gap. The force applied by the user toward the gumline causes the device to gradually move towards the gumline along the inner periphery 28 of the flossing head 26. Forceful impingement of the floss 14 into the gums is prevented by maintaining the contact between teeth and the inner periphery 28 of the flossing head 26 while moving the floss 14 towards the gumline.

Alternatively, the third acute angle C provides a second braking surface which can be used for inserting the floss 14 between the teeth at the opposing end of the flossing arch 30.

Although the present invention is designed to allow flossing of the entire dental arch, its main target is on the three rear teeth on each side of both the upper and lower rows of teeth. In dental numbering parlance, the present invention targets the teeth numbered 1, 2, 3, 14, 15, 16, 17, 18, 19, 30, 31 and 32.

The insertion of the floss 14 into the gaps between the molars is accomplished from the side of the mouth. The first acute angle A of the present invention permits insertion of the floss 14 and floss head 26 into the area between the teeth without causing the user to extend the lower jaw to an uncomfortable position.

Additionally, the fourth acute angle D shortens the extension of the flossing head 26 into the mouth without causing further discomfort to the user. The brake is again utilized when inserting the floss 14 between the molars to avoid impingement of the floss 14 into the gums. The floss 14 and flossing device 10 now resides in the same plane as the gap between the teeth. This co-planer relationship improves the cleaning ability of the present invention. Furthermore, the first acute angle A of the device allows the user to leave the device 10 in the flossing position during the duration of the flossing process without experiencing any discomfort.

Upon insertion, the flossing device 10 is now in a position to provide flossing and cleaning of teeth around the gumlines. The floss 14 is manipulated by finger tip control of the control pad 24. The control pad 24 permits the up and down movement of the floss 14 around the teeth and gumlines. This is accomplished primarily because the user's hand now resides outside of the mouth and on the control pad 24. Additionally, the length of the floss 14 permits a wrap around effect on the teeth wherein the sides of the teeth may be cleaned by the present invention. The woven nylon floss 14 serves to provide a larger cleaning profile. After completing the flossing of a particular gap, the device and the floss 14 is removed from one gap and inserted into the next until all of the teeth have been cleaned.

The present invention also includes a debrider implement 16 at the opposing end of the device 10. The debrider implement 16 permits the sub-gingival tracing around each tooth. The sub-gingival tracing removes food, bacteria, and plaque from below the gumline. This form of cleaning around the teeth can prevent the build up of tartar and also reduces the formation of periodontal pockets. The debrider 16 also serves as a pick to dislodge material caught between teeth.

In the present invention, the tracing operation is also accomplished through the use of the control pad 24. The control pad 24 is gripped by the user with the debrider implement 16 directed towards the teeth. The tip end point 38 of the debrider implement 16 is inserted around the teeth beneath the gumline and is used to trace around each tooth. The manipulation of the debrider implement around each tooth removes food, bacteria and plaque from under the gumline. The material can then be washed away by regular brushing or rinsing of the mouth.

An alternative embodiment of the debrider implement 16 includes debriding grooves 42. The debriding grooves 42 are utilized to disturb the material loosened during the tracing operation. The debriding grooves 42 function to break loose and collect the material within the groove 42 as opposed to just pushing the material around with the debrider implement. The collected material is removed either by wiping off the end of the debrider implement 16 or by rinsing it under water. Tracing should be done around each tooth just as in flossing.

The shoulders 40 of the debrider implement 16 prevent the debrider end 20 from getting stuck or lodged between the teeth during the tracing operation or while using the implement 16 as a pick. The wider shoulders 40 will not allow over insertion of the end of the debrider implement 16 into the gaps between the teeth.

Upon completion of the flossing and tracing by the user the entire flossing and debrider device 10 is then disposed.

The nylon used in the present invention for the floss 14 is hydrophilic. Therefore certain compounds may be added to the nylon in order to provide additional benefits to the user of the device 10. Fluoride can be added to the nylon to strengthen the tooth surfaces. Additionally, an antimicrobial can be added to kill the bacteria during the flossing operation. The antimicrobial will kill bacteria on contact and have a residual effect on new bacteria between cleaning. Flavored floss may also be added to the present invention in order to make the flossing operation more pleasant to the user.

In accordance with the provisions of the patent statutes, the present invention has been described in what is considered to represent its preferred embodiment. However, it should be noted that the invention can be practiced otherwise than as specifically illustrated and described without departing from its spirit and scope.

What is claimed is:

1. A disposable dental hygiene device for flossing and tracing around teeth, comprising:
   (a) a linear frame having a flossing end, a debrider end, and a linear base edge extending between said debrider end and said floss end;
   (b) a control pad extending from the linear frame in a co-planer manner;
   (c) a debrider implement formed at the debrider end of said frame;
   (d) a flossing head formed at the flossing end of said frame;
   (e) an inner periphery of said flossing head and said control pad forming a flossing arch; and
   (f) floss extending from an outer edge of said control pad to an outer edge of said flossing head across said flossing arch, a first acute angle of 28–32 degrees is formed at the intersection of the base edge extended and the floss line extended, a second acute angle is formed at the intersection of the floss and the inner periphery of said flossing head, said second acute angle is greater than the first acute angle, said second acute angle creating a brake with the inner periphery of said flossing head to prevent direct impingement of said floss onto the gums during insertion of said floss between teeth, said floss and said debrider implement manipulated around teeth through the fingertip control of said control pad.

2. A disposable dental hygiene device as recited in claim 1, wherein the debrider implement further comprises an upper and a lower edge and an end point, said upper and lower edge each having debriding grooves extending along each edge to the end point of the debrider implement.

3. A disposable dental hygiene device as recited in claim 1, wherein said frame and control pad are made of biodegradable material.

4. A disposable dental hygiene device as recited in claim 3, wherein the biodegradable material is plastic.

5. A disposable dental hygiene device as recited in claim 1, wherein the floss is woven nylon.

6. A disposable dental hygiene device as recited in claim 5, wherein the floss contains an anti-microbial.

7. A disposable dental hygiene device as recited in claim 5, wherein the floss contains fluoride.

8. A disposable dental hygiene device as recited in claim 1, wherein a second brake is created by a third acute angle formed at the intersection of an inner periphery of said control pad and said floss.

9. A disposable dental hygiene device as recited in claim 1, wherein said flossing head extends downward from said base edge creating a fourth acute angle, said fourth acute angle resulting in a shorter distance between said flossing head and said control pad.

10. A disposable dental hygiene device for flossing and tracing around teeth, comprising:
    (a) a linear frame having a base edge, a flossing end, and a debrider end;
    (b) a control pad extending from the linear frame in a co-planer manner;
    (c) a debrider implement formed at the debrider end of said frame, said debrider implement having an upper and a lower edge and an end point, said upper and lower edge each having debriding grooves extending along each edge to the end point of said tracing implement;
    (d) a flossing head formed at the flossing end of said frame;
    (e) an inner periphery of said flossing head and said control pad forming a flossing arch; and
    (f) floss extending from an outer edge of said control pad to an outer edge of said flossing head across said flossing arch, a first acute angle of 28–32 degrees is formed at the intersection of the base edge extended and the floss line extended, a second acute angle is formed at the intersection of the floss and the inner periphery of said flossing head, said second acute angle is greater than the first acute angle, said second acute angle creating a brake with the inner periphery of said flossing head to prevent direct impingement of said floss onto the gums during insertion of said floss between teeth, said floss and said debrider implement manipulated around teeth through the fingertip control of said control pad.

11. A disposable dental hygiene device as recited in claim 10, wherein said frame and control pad are made of biodegradable material.

12. A disposable dental hygiene device as recited in claim 10, wherein the floss is woven nylon.

13. A disposable dental hygiene device as recited in claim 10, wherein the floss contains an anti-microbial.

14. A disposable dental hygiene device as recited in claim 10, wherein the floss contains fluoride.

15. A disposable dental hygiene device as recited in claim 10, wherein a second brake is created by a third acute angle formed at the intersection of an inner periphery of said control pad and said floss.

16. A disposable dental hygiene device as recited in claim 10, wherein said flossing head extends downward from said base edge creating a fourth acute angle, said fourth acute angle resulting in a shorter distance between said flossing head and said control pad.

17. A disposable dental hygiene device for flossing and tracing around teeth, comprising:
    (a) a linear frame having a flossing end, a debrider end, and a linear base edge extending between said debrider end and said floss end;

(b) a control pad extending from the linear frame in a co-planer manner;

(c) a debrider implement formed at the debrider end of said frame, the debrider implement having an upper and a lower edge and an end point, said upper and lower edge each having debriding grooves extending along each edge to the end point of the debrider implement;

(d) a flossing head formed at the flossing end of said frame;

(e) an inner periphery of said flossing head and said control pad forming a flossing arch; and (f) floss extending from an outer edge of said control pad to an outer edge of said flossing head across said flossing arch, a first acute angle is formed at the intersection of the base edge extended and the floss line extended, a second acute angle is formed at the intersection of the floss and the inner periphery of said flossing head, said second acute angle is greater than the first acute angle, said second acute angle creating a brake with the inner periphery of said flossing head to prevent direct impingement of said floss onto the gums during insertion of said floss between teeth, said floss and said debrider implement manipulated around teeth through the fingertip control of said control pad.

18. A disposable dental hygiene device as recited in claim 17, wherein said frame and control pad are made of biodegradable material.

19. A disposable dental hygiene device as recited in claim 17, wherein a second brake is created by a third acute angle formed at the intersection of an inner periphery of said control pad and said floss.

20. A disposable dental hygiene device as recited in claim 17, wherein said flossing head extends downward from said base edge creating a fourth acute angle, said fourth acute angle resulting in a shorter distance between said flossing head and said control pad.

* * * * *